(12) United States Patent
Ruan et al.

(10) Patent No.: US 9,128,054 B2
(45) Date of Patent: Sep. 8, 2015

(54) DETECTION METHOD FOR AN ION MIGRATION SPECTRUM AND AN ION MIGRATION SPECTROMETER USING THE SAME METHOD

(75) Inventors: Ming Ruan, Beijing (CN); Peng Jiao, Beijing (CN); Yingrong Jian, Beijing (CN); Yangtian Zhang, Beijing (CN); Jin Lin, Beijing (CN); Hua Peng, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 13/560,440

(22) Filed: Jul. 27, 2012

(65) Prior Publication Data

US 2012/0326024 A1    Dec. 27, 2012

Related U.S. Application Data

(63) Continuation-in-part of application No. 12/437,907, filed on May 8, 2009, now abandoned.

(30) Foreign Application Priority Data

May 9, 2008  (CN) .......................... 2008 1 0106169

(51) Int. Cl.
*G01N 27/62*   (2006.01)
(52) U.S. Cl.
CPC .................................... *G01N 27/622* (2013.01)
(58) Field of Classification Search
CPC .................................................. G01N 27/622
USPC ................................................ 250/281–300
See application file for complete search history.

(56) References Cited

U.S. PATENT DOCUMENTS 5,475,217 A * 12/1995 Bradshaw ..................... 250/287
5,633,997 A    5/1997 Barber et al.
(Continued)

FOREIGN PATENT DOCUMENTS

WO    WO-2007/120931 A1    10/2007

OTHER PUBLICATIONS

International Search Report in PCT/CN2009/000497 dated Aug. 20, 2009.
(Continued)

*Primary Examiner* — Robert Kim
*Assistant Examiner* — Eliza Osenbaugh-Stewar
(74) *Attorney, Agent, or Firm* — Marshall, Gerstein & Borun LLP

(57) ABSTRACT

A detection apparatus and method for an ion migration spectrum include acquiring an ion migration spectrum of pure carrier gas and an ion migration spectrum of carrier gas containing a test substance sample and performing differential process on the ion migration spectrum of the pure carrier gas and the ion migration spectrum of the carrier gas containing the test substance sample to acquire a differential spectrum. The value of a characteristic peak of the differential spectrum represents properties of the sample of substances. The method avoids interferences on the migration spectrum from interference sources of the apparatus itself, thereby improving detection sensitivity and accuracy of the ion migration spectrum, and migration spectrum shift caused by variations in the environmental conditions can be found and corrected through the differential process on the migration spectrum of the pure carrier gas, thereby achieving self-stableness and self-correction of the ion migration spectrometer.

17 Claims, 3 Drawing Sheets

(56) References Cited

U.S. PATENT DOCUMENTS

| | | | |
|---|---|---|---|
| 6,495,824 B1 | 12/2002 | Atkinson | |
| 7,233,870 B1 | 6/2007 | Dalrymple | |
| 2003/0209665 A1* | 11/2003 | Losch et al. | 250/287 |
| 2005/0133710 A1* | 6/2005 | Losch et al. | 250/282 |
| 2005/0253061 A1* | 11/2005 | Cameron et al. | 250/287 |
| 2007/0228269 A1 | 10/2007 | Miller et al. | |
| 2007/0277589 A1* | 12/2007 | Harden et al. | 73/31.03 |
| 2008/0001079 A1 | 1/2008 | Wang et al. | |
| 2008/0185512 A1* | 8/2008 | Miller et al. | 250/287 |
| 2008/0255769 A1 | 10/2008 | Zhou et al. | |
| 2009/0212207 A1 | 8/2009 | Griffin et al. | |

OTHER PUBLICATIONS

Roehl, "Ion Mobility Spectrometry (IMS)—A Chemical Separation Technique Using an Electrostatic Field;" 1989, Industry Application Society Annual Meeting, Conference Record of the 1989 IEEE, vol. 2, p. 2190-2195.

* cited by examiner

DETECTION METHOD FOR AN ION MIGRATION SPECTRUM AND AN ION MIGRATION SPECTROMETER USING THE SAME METHOD

RELATED APPLICATION

This application is a continuation-in-part of U.S. patent application Ser. No. 12/437,907, filed May 8, 2009, which claims priority to Chinese Patent Application No. 200810106169.X, filed May 9, 2008, both of which are incorporated herein by reference.

TECHNICAL FIELD

This invention relates to an ion migration spectrometer (IMS) and a detection method for an ion migration spectrum used therein, in particular relates to a detection method for an ion migration spectrum which performs differential peak search and an ion migration spectrometer using this method.

BACKGROUND TECHNOLOGY

The detection technique for an ion migration spectrum was firstly proposed by Karasek and Cohen as a method for analyzing organic compounds in 1970. From the beginning, the IMS has already aroused people's strong interest, however, until the end of the 1980s, did people begin to grasp some difficulties in the IMS such as the process of molecular chemical ionization under the atmospheric pressure (APCI), thereby greatly improving the performance of the IMS which is then broadly applied to various aspects. At present, the products based on IMS have been widely used for detecting exploders, drugs, chemical reagents at the airport, dock, station, etc. The IMS has become one of the existing broadly-used technologies for detecting trace chemicals due to its advantages of high sensitivity (10-8 to 10-14 g), short analysis time, strong function, and not too high cost, etc.

FIGS. 1 and 2 illustrate a structural diagram of a conventional IMS system and its front end (namely a migration tube) respectively. As illustrated in FIG. 1, the conventional IMS system is comprised of a sampling system 101 for sampling; a carrier gas preparation system 102 and a carrier gas exhausting system 103 for preparing carrier gas and exhausting carrier gas, respectively; a migration gas preparation system 104 and a migration gas exhausting system 105 for preparing migration gas and exhausting migration gas respectively; a migration tube 106 as the core part of the IMS system; an ion gate of the migration tube 106 and a controller 107; a high-pressure generator and controller 108 and a temperature sensor and controller 109; and a migration spectrum detector 110. The migration spectrum detector 110 comprises a micro-current amplifier 1101 for amplifying the current detected by a charge sensor 206 in the migration tube 106, an A/D converter 1102 for digitizing the amplified current value; and a migration spectrum acquirement device 1103 for performing calibration on the digitized current signals to acquire an eventual migration spectrum.

As illustrated in FIG. 2, the migration tube 106 mainly comprises a gasifier 201, an ion source 202, a reaction region 203, an ion gate 204, a drift region 205, a charge sensor 206, a sample inlet 211, a carrier gas inlet 212 and outlet 213, a migration gas inlet 214 and outlet 215. The basic operation principles of the IMS are described as follows:

1. A sample (solid sample or gas sample) containing suspect substances enters into the migration tube 106 via the sampling system 101.

2. After the sample has been gasified by gasifier 201, molecules of the suspect substances enter into the ion source 202 and are ionized into molecular ions.

3. The mixed ions are introduced into the reaction region 203 via an electrical field where the molecular ions have been fully reacted with each other.

4. The ion gate 204 is initiated to cause the ions to drift in the drift region 205 with a constant electric field intensity which is filled with gas.

5. The charge sensor 206 senses time for the ions to pass through the drift region.

6. The time for different ions to pass through the drift region 205 to the charge sensor 206 is different due to the different characteristics of the ions, thus, the arrival time of the charges detected by the charge sensor 206 is related to the characteristics of the ions, so the migration spectrum detector 110 can acquire a one-dimensional time ion migration spectrum related to the characteristics of the ions by processing the detection results of the charge sensor 206.

7. Various processing are performed on the ion migration spectrum and a characteristic ion peak of the suspect substance is identified from the ion migration spectrum via a software algorithm, so that an appropriate alarm information can be generated accordingly.

Since the ion migration spectrum is easily interfered by the peaks of various interference substance, the pressure and temperature of the atmosphere, and the ion migration spectrum is complicated by the mechanical vibration, electronics noise and so on. So, the key for improving detection sensitivity and accuracy of the suspect substances by the ion migration spectrometer and reducing the false alarm rate is to find the characteristic ion migration peak of the suspect substance accurately and efficiently and to eliminate various interferences as much as possible. Currently, there are various methods for processing and seeking a ion migration peak. However, there is no good way to eliminate various interferences and find the characteristic ion migration peak of the suspect substance accurately and efficiently.

Thus, what is desired is an improved method for performing spectrum process and peak search on the ion migration spectrum, eliminating various interferences, seeking a characteristic ion migration peak of the suspect substance accurately and efficiently, improving detection sensitivity and accuracy of the suspect substance by the ion migration spectrometer and reducing the false alarm rate, as well as an ion migration spectrometer using the method.

Contents of the Invention

The applicant has found that an ion source in an ion migration spectrometer provides an approximately stable charge source. When the atmosphere pressure, temperature and electrical field are constant, the total charge amount entering into the reaction region of the system is substantially unchanged after the carrier gas has been ionized, no matter the carrier gas is pure carrier gas or gas mixed with samples or interference substances. Likewise, the total charge amount of the molecular ions arriving at the charge sensor is almost constant after the molecular ions exchange charge each other and pass through the drift region. Certainly, the structure of the migration spectrum can be changed according to the ion characteristic differences.

Considering the above characteristics of the ion migration spectrometer, if a differential process is performed on the ion migration spectrum of the pure carrier gas and the gas mixed with samples (which is also referred as sample gas in the description hereafter), it will eliminate difficulties and errors brought by various interference sources to the spectrum process and peak search of the migration spectrum (because the intensity and structure of many interference sources do not have significant change during a short period of time), highlight the specific structure of the ion migration spectrum of the sample gas, facilitate subsequent spectrum process and peak search, improve the detection sensitivity and accuracy for the suspect substance by the ion migration spectrometer, and reduce the false alarm rate at the same time.

Thus, this invention provides a differential method for performing process and peak search on an ion migration spectrum which can seek a characteristic peak of ion migration spectrum of the suspect substance accurately and efficiently, improve the sensitivity and accuracy of the detection of the suspect substance by the ion migration spectrometer, and reduce the false alarm rate.

According to one aspect of this invention, there is provided a detection method for an ion migration spectrum, comprising steps of: acquiring an ion migration spectrum of pure carrier gas; acquiring an ion migration spectrum of carrier gas containing a test substance sample; and performing differential process on the ion migration spectrums of the pure carrier gas and the carrier gas containing the test substance sample to acquire a differential spectrum, wherein the value of a characteristic peak of said differential spectrum and a change of the value of the characteristic peak over time are used to determine the properties of said test substance sample.

According to another aspect of this invention, there is provided an ion migration spectrum detector, comprising: a migration spectrum acquirement device for acquiring the migration spectrums of carrier gas containing a test substance sample and the pure carrier gas respectively, said ion migration spectrum detector further comprises a differential spectrum acquirement device for performing differential process on the migration spectrums of said pure carrier gas and the carrier gas containing the test substance sample to acquire a differential spectrum, wherein the value of a characteristic peak of said differential spectrum and a change of the value of the characteristic peak over time are used to determine properties of said test substance sample.

According to another aspect of this invention, there is provided an ion migration spectrometer comprising the above mentioned ion migration spectrum detector.

Compared with the prior art, this invention can avoid difficulties and errors brought by various interference sources of the apparatus itself to the spectrum process and peak search on the migration spectrum, highlights the specific structure of the ion migration spectrum of the test substance, seeks the characteristic peak of the ion migration spectrum of the harmful substance more accurately and fast, thereby it improves the sensitivity and accuracy of detecting the suspect substance by the ion migration spectrometer, and reduces the false alarm rate at the same time.

Furthermore, this invention mainly relates to process the detected migration spectrum to seek the characteristic peak of the ion migration spectrum of the suspect substance more accurately and fast, therefore, it is not required to modify the ion migration spectrometer, thus it can be seen that this invention can be adapted to improve detection sensitivity and accuracy of the ion migration spectrometer at a relatively low cost. This invention is also applicable to all the technical fields of developing and manufacturing the ion migration spectrometer.

DESCRIPTION OF FIGURES

Other various advantages and benefits will become apparent for those skilled in the art after reading detailed description of the following preferred embodiments. The drawings are only used for illustrating the preferred embodiments, which are not intended as limitations to this invention. Moreover, the corresponding reference signs are used to represent the corresponding components throughout the drawings. In the drawings.

SPECIFIC EMBODIMENTS

This invention will be further described by combining the drawings and specific embodiments.

Figure 1:
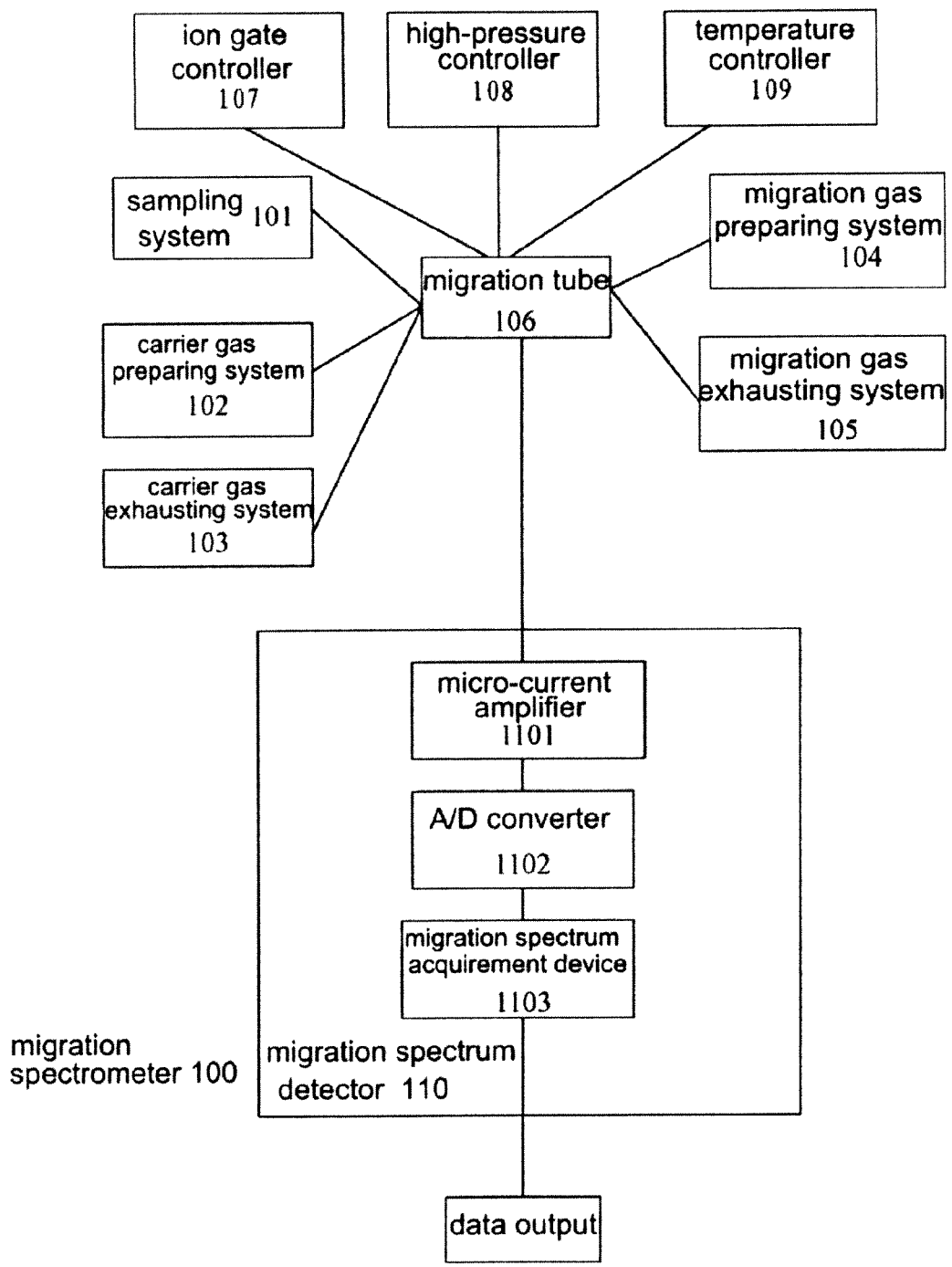
FIG. 1 illustrates a structural diagram of a system of a conventional ion migration spectrometer.
Figure 2:
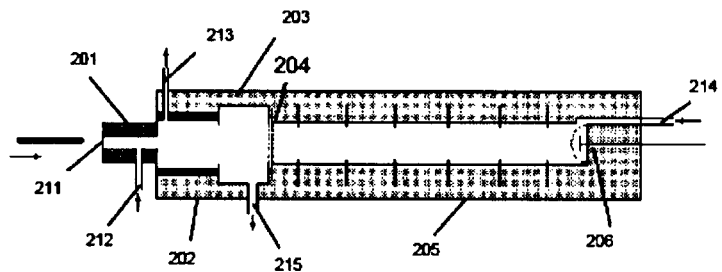
FIG. 2 illustrates a structural diagram of a migration tube in the conventional ion migration spectrometer.
Figure 3:
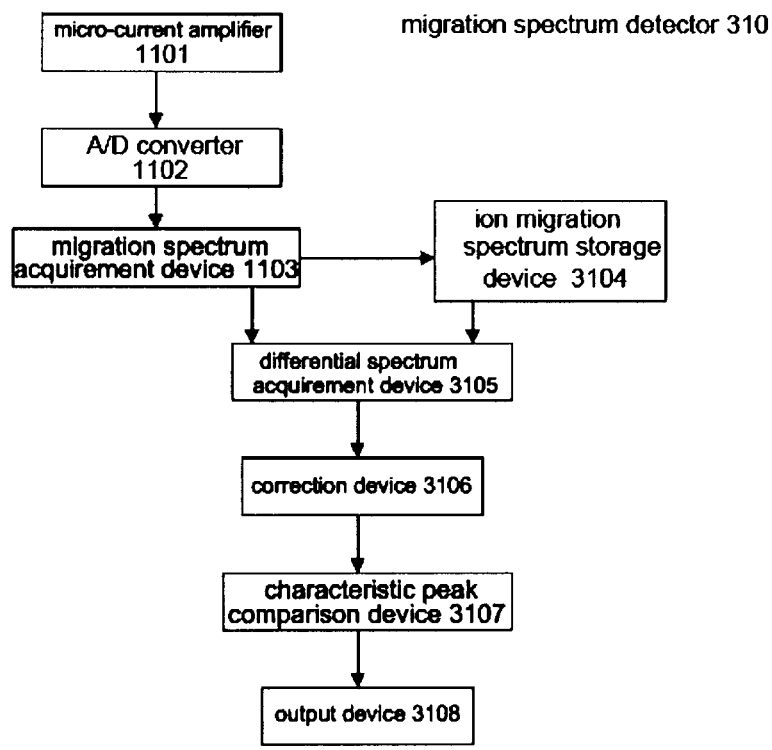
FIG. 3 shows a structural diagram of a migration spectrum detector according to a preferred embodiment of this invention.

FIG. 3 shows a structural diagram of a migration spectrum detector 310 according to a preferred embodiment of this invention. The migration spectrum detector 310 can be used in the conventional migration spectrometer 100 to substitute the migration spectrum detector 110 shown in FIG. 1 to improve detection sensitivity and accuracy of the conventional migration spectrometer. Therefore, the migration spectrum detector 310 can be used in connection with a migration tube shown in FIG. 2 completely.

As shown in FIG. 3, the migration spectrum detector 310 further comprises an ion migration spectrum storage 3104 and a differential spectrum acquirement device 3105 in addition to the micro-current amplifier 1101, the A/D converter 1102 and the migration spectrum acquirement device 1103 in the conventional migration spectrum detector 110. Certainly, as long as the migration spectrum can be acquired, all the other components which can achieve the functions of the micro-current amplifier 1101, the A/D converter 1102 and the migration spectrum obtaining device 1103 are also possible and within the protection scope of this invention. The ion migration spectrum storage 3104 is used to store a migration spectrum of pure carrier gas and a migration spectrum of carrier gas containing a test substance sample acquired by the migration spectrum acquirement device 1103 respectively. The differential spectrum acquirement device 3105 performs differential process on the migration spectrum of the pure carrier gas and the migration spectrum of the carrier gas containing the test substance sample to acquire a differential spectrum, and also performs processes of smoothing and peak search on the differential spectrum to acquire a characteristic peak of the differential spectrum that characterizes the test substance sample. Optionally, the migration spectrum detector 310 further comprises: a differential spectrum correction device 3106 for correcting the acquired peak position according to the conditions of the environment where the ion migration spectrometer is located; a characteristic peak comparison device 3107 for comparing the acquired characteristic peak that characterizes the test substance sample with characteristic peaks in a characteristic peak storage of dangerous substances to determine whether the test substance sample contains the dangerous substances; and an output device 3108 for outputting a detection result for the test substance sample.

Optionally, during the sampling for the migration spectrum of the carrier gas containing the test substance sample, the migration spectrum acquirement device 1103 can acquire multiple successive migration spectrums of the carrier gas over time. Subsequently the differential spectrum acquirement device 3105 may perform differential process between each of the multiple successive migration spectrums of the carrier gas and the migration spectrum of the pure carrier gas respectively, so as to acquire the corresponding successive differential spectrums. Then characteristic peak comparison device 3107 determines the change tendency of the characteristic peak over time by comparing the values of this specific characteristic peak in each of the successive differential spectrums. For example, if the value of the characteristic peak gradually increase to a maximum value and then decreases over time, then characteristic peak comparison device 3107 can further judge the test substance sample contains the dangerous substance represented by the characteristic peak. If the value of the characteristic peak directly gradually decreases even to zero according to the change tendency, then characteristic peak comparison device 3107 can further judge the test substance sample does not contain the dangerous substance represented by the characteristic peak. It is because that it will take time for the ion to arrive at the drift region, thereby fewer ions pass through the drift region at the beginning of the sampling, which causes the relatively lower characteristic peak value for the specific ion; As time goes on, even more ions arrives at and passes through the drift region, which contributes to the increasing in the characteristic peak value; Subsequently with most of the ions have passed through the drift region, the characteristic peak value decrease gradually. As can be seen, if the value of the characteristic peak directly decreases without increasing, it is very likely that the characteristic peak represents the impurity in the drift region instead of the substance in the test substance sample, i.e. the properties of the test substance sample. That is, the test substance sample does not contain the substance represented by the characteristic peak.

By leveraging the characteristic peak value of the differential spectrum along with the change tendency of the characteristic peak value over time, the dangerous substance in the test substance sample can be further accurately determined. Such dangerous substance determination is more insusceptible to the interference of the sampling (or detection) surroundings.

Furthermore, in the migration spectrum detector 310, the migration spectrum acquirement device 1103 can acquire the migration spectrums of the pure carrier gas for many times, while the differential spectrum acquiring device 3105 can perform the differential process on the acquired migration spectrums of the pure carrier gas to find and correct a migration spectrum shift caused by variations in the environmental conditions, thereby achieving self-stableness and self-correction of the ion migration spectrometer.

The migration spectrum detector 310 eliminates the impact on the migration spectrum from the interference sources of the detector or spectrometer itself by means of performing the differential process on the migration spectrum of the pure carrier gas and the migration spectrum of the carrier gas containing the test substance sample, thereby improving sensitivity and accuracy of the apparatus.

Figure 4:
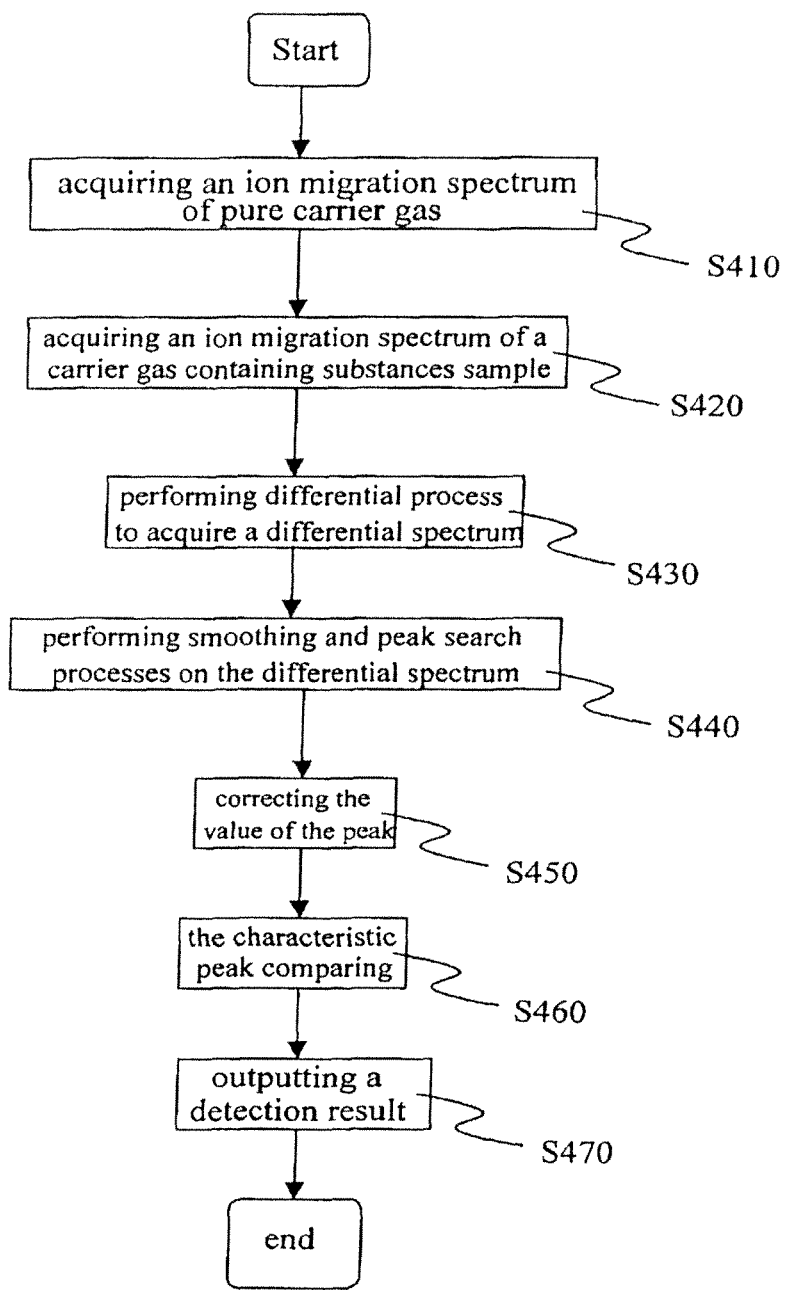
FIG. 4 shows a detection method for an ion migration spectrum according to a preferred embodiment of this invention.

FIG. 4 shows a flow chart of a detection method for a ion migration spectrum executed by the migration spectrum detector 310 in detail.

In step S410, the migration spectrum acquirement device 1103 acquires the migration spectrum ($A_i$, $i=1, 2, 3, \ldots$) of the pure carrier gas, and optionally, stores the acquired migration spectrum of the pure carrier gas in the ion migration spectrum storage 3104. In step S420, the migration spectrum acquirement device 1103 acquires the migration spectrum ($B_i$, $i=1, 2, 3, \ldots$) of the carrier gas containing a test substance sample, and optionally, stores the acquired migration spectrum of the carrier gas containing the test substance sample in the ion migration spectrum storage 3104. In step S430, the differential spectrum acquirement device 3105 performs the differential process on the ion migration spectrum of the pure carrier gas and the ion migration spectrum of the carrier gas containing the test substance sample to acquire a differential spectrum ($C_i$, $i=1, 2, 3, \ldots$). In step S440, the processes of smoothing and peak search are performed on the differential spectrum $C_i$ in the differential spectrum acquirement device 3105 ($H_j=F(C_i)$, $j=1, 2, 3, \ldots$, wherein $H_j$ represents the smoothed differential spectrum). These processes, including the differential process, smoothing and peak search can adopt any methods in the existing technology of spectrum analysis. Then, optionally, said method further comprises step S450, wherein the acquired peak position and the differential spectrum $H_j$ are corrected by the differential spectrum correction device 3106 according to the condition of the environment where the ion migration detector 310 or spectrometer is located; step S460, wherein the acquired characteristic peak that represents the test substance sample is compared with the characteristic peaks in the characteristic peak storage of dangerous substances to determine whether the test substance sample contains dangerous substances; and step S470, in which the detection result of the test substance sample is outputted.

Optionally, in step S420, the migration spectrum acquirement device 1103 can acquire multiple successive migration spectrums of the carrier gas over time. Accordingly, in step S440, the differential spectrum acquirement device 3105 may perform differential process between each of the multiple successive migration spectrums of the carrier gas and the migration spectrum of the pure carrier gas respectively, so as to acquire the corresponding successive differential spectrums. Then in step S460, the change tendency of the characteristic peak value over time is determined by comparing the values of this specific characteristic peak in each of the successive differential spectrums. For example, if the value of the characteristic peak gradually increase to a maximum value and then decreases over time, it can be further judged that the test substance sample contains the dangerous substance represented by the characteristic peak. If the value of the characteristic peak directly gradually decreases even to zero according to the change tendency, then it can be further judged that the test substance sample does not contain the dangerous substance represented by the characteristic peak. It is because that it will take time for the ion to arrive at the drift region, thereby fewer ions pass through the drift region at the beginning of the sampling, which causes the relatively lower characteristic peak value for the specific ion; As time goes on, even more ions arrives at and passes through the drift region, which contributes to the increasing in the characteristic peak value; Subsequently, with most of the ions have passed through the drift region, the characteristic peak value decrease gradually. As can be seen, if the characteristic peak value directly decreases without increasing, it is very likely that the characteristic peak represents the impurity in the drift region instead of the substance in the test substance sample, i.e. the properties of the test substance sample. That is, the test substance sample does not contain the substance represented by the characteristic peak.

By leveraging the characteristic peak value of the differential spectrum along with the change tendency of the characteristic peak value over time, the dangerous substance in the test substance sample can be further accurately determined.

Such dangerous substance determination is more insusceptible to the interference of the sampling (or detecting) surroundings.

In the differential process at step S430, no matter which solution is adopted, i.e., whether it is a solution of forward difference, backward difference or difference for many times, it belongs to the protection scope of this invention.

In said method, the migration spectrums of the pure carrier gas can be further acquired for many times and the differential process on the acquired ion migration spectrums of the pure carrier gas can be performed for many times to find the migration spectrum shift caused by variations in the environmental conditions and correct said shift, thereby achieving self-stableness and self-correction of the ion migration spectrometer.

It should be noted that the components in the migration spectrum detector 310 are logically divided according to the functions to be performed, however, this invention is not limited to this, the respective components in the migration spectrum detector 310 can be re-divided or combined according to the requirement, for example, some components can be combined into a single one, or some components can be further divided into more sub-components.

Embodiments of the present invention may be implemented in hardware, or as software modules running on one or more processors, or in a combination thereof. That is, those skilled in the art will appreciate that a microprocessor or digital signal processor (DSP) may be used in practice to implement some or all of the functionality of some or all components of the migration spectrum detector according to an embodiment of the present invention. The invention may also be embodied as one or more device or apparatus programs (e.g. computer programs and computer program products) for carrying out part or all of any of the methods described herein. Such programs embodying the present invention may be stored on computer-readable media, or could, for example, be in the form of one or more signals. Such signals may be data signals downloadable from an Internet website, or provided on a carrier signal, or in any other form.

It should be noted that the aforesaid embodiments are illustrative of this invention instead of restricting this invention, substitute embodiments may be designed by those skilled in the art without departing from the scope of the claims enclosed. In the claims, any reference symbols located between the parentheses should not constitute restrictions to the claims. The word "include" does not exclude elements or steps which are present but not listed in the claims. The word "a" or "one" preceding the elements does not exclude the presence of a plurality of such elements. This invention can be achieved by means of hardware including several different elements or by means of a suitably programmed computer. In the unit claims that list several means, several ones among these means can be specifically embodied via the same hardware item. The use of such words as first, second, third does not represent any order, which can be explained as names.

The invention claimed is:

1. A detection method of an ion migration spectrum, comprising steps of:
   acquiring an ion migration spectrum of a pure carrier gas;
   acquiring an ion migration spectrum of a carrier gas containing a test substance sample; and
   performing differential process on the ion migration spectrum of said pure carrier gas and the ion migration spectrum of the carrier gas containing a test substance sample to acquire a differential spectrum, wherein a value of a characteristic peak of said differential spectrum and a change of the value of the characteristic peak over time, which is calculated by comparing the values of the characteristic peak in successive differential spectrums, are used to determine properties of said test substance sample.

2. The method as claimed in claim 1, further comprising a step of:
   performing smooth and peak search process on said differential spectrum to acquire the value of the characteristic peak of said differential spectrum.

3. The method as claimed in claim 1, further comprising a step of:
   comparing the characteristic peak of said differential spectrum with characteristic peaks in a characteristic peak storage of dangerous substances to determine whether said test substance sample contains the dangerous substances.

4. The method as claimed in claim 1, further comprising a step of:
   correcting the characteristic peak of said differential spectrum according to the environmental conditions.

5. The method as claimed in claim 1, further comprising a step of:
   storing the ion migration spectrum of said pure carrier gas and the ion migration spectrum of the carrier gas containing the test substance sample.

6. The method as claimed in claim 1, further comprising steps of:
   acquiring the ion migration spectrums of the pure carrier gas for multiple times, and performing the differential process on the multiple acquired ion migration spectrums of the pure carrier gas to find and correct the shift of said ion migration spectrum.

7. A non-transitory computer program product executed on a computer processor, the computer program product carrying out the method according to claim 1, wherein the differential process is executed by the computer processor.

8. The non-transitory computer program product of claim 7 stored on a non-transitory recording media having instructions stored therein for implementing the steps of the method when the instructions are executed by a computer processor.

9. The method of claim 1, further comprising a step of:
   determining that the test substance sample contains a substance corresponding to the characteristic peak if the characteristic peak increases to a maximum and then decreases over time.

10. The method of claim 1, further comprising the step of:
    determining that the test substance sample does not contain a substance corresponding to the characteristic peak if the characteristic peak decreases over time without increasing.

11. An ion migration spectrum detector, comprising a migration spectrum acquirement device for acquiring a migration spectrum of carrier gas containing a test substance sample and a migration spectrum of pure carrier gas, said ion migration spectrum detector further comprising:
    a differential spectrum acquirement device for performing differential process on the migration spectrum of said pure carrier gas and the migration spectrum of the carrier gas containing the test substance sample to acquire a differential spectrum, wherein the value of a characteristic peak of said differential spectrum and a change of the value of the characteristic peak over time, which is calculated by comparing the values of the characteristic peak in successive differential spectrums, are used to determine properties of said test substance sample.

12. The ion migration spectrum detector as claimed in claim 11, wherein said differential spectrum acquirement device performs smoothing and peak search process on said differential spectrum to acquire the value of the characteristic peak value of said differential spectrum.

13. The ion migration spectrum detector as claimed in claim 11, further comprising:
 a characteristic peak comparison device for comparing the characteristic peak of said differential spectrum with characteristic peaks in a characteristic peak storage of dangerous substances to determine whether said test substance sample contains the dangerous substances.

14. The ion migration spectrum detector as claimed in claim 11, further comprising:
 a differential spectrum correction device for correcting the characteristic peak of said differential spectrum according to the environmental conditions.

15. The ion migration spectrum detector as claimed in claim 11, further comprising:
 an ion migration spectrum memory for storing the ion migration spectrum of said pure carrier gas and the ion migration spectrum of the carrier gas containing the test substance sample.

16. The ion migration spectrum detector as claimed in claim 11, wherein said migration spectrum acquiring device acquires the migration spectrums of the pure carrier gas for multiple times, and performs the differential process on the multiple acquired migration spectrums of the pure carrier gas to find and correct the shift of said ion migration spectrum.

17. An ion migration spectrometer, comprising
 a carrier gas preparation system and a carrier gas exhausting system for preparing carrier gas and exhausting carrier gas, respectively;
 a migration gas preparation system and a migration gas exhausting system for preparing migration gas and exhausting migration gas, respectively;
 a migration tube, in which the gas migration is performed; and
 the ion migration spectrum detector claimed in claim 11.

* * * * *